(12) United States Patent
Ruskin

(10) Patent No.: US 12,562,261 B1
(45) Date of Patent: Feb. 24, 2026

(54) HEALTHCARE COMMUNICATIONS SYSTEM GENERATING CHATBOT CONVERSATION BASED MEDICAL SUPPLY STOCKING LIST AND RELATED METHODS

(71) Applicant: Inmar Clearing, Inc., Winston-Salem, NC (US)

(72) Inventor: Grazia Ruskin, Austin, TX (US)

(73) Assignee: INMAR CLEARING, INC., Winston-Salem, NC (US)

( * ) Notice: Subject to any disclaimer, the term of this patent is extended or adjusted under 35 U.S.C. 154(b) by 145 days.

(21) Appl. No.: 18/379,620

(22) Filed: Oct. 12, 2023

(51) Int. Cl.
*G16H 40/20* (2018.01)
*G16H 10/60* (2018.01)

(52) U.S. Cl.
CPC ............. *G16H 40/20* (2018.01); *G16H 10/60* (2018.01)

(58) Field of Classification Search
CPC ............................... G16H 40/20; G16H 10/60
USPC .......................................................... 705/2, 3
See application file for complete search history.

(56) References Cited

U.S. PATENT DOCUMENTS

| | | | |
|---|---|---|---|
| 7,289,825 B2 | 10/2007 | Fors et al. | |
| 9,070,282 B2 | 6/2015 | Clough | |
| 11,929,963 B1 * | 3/2024 | Zheng ........................ | G06F 8/77 |
| 2007/0073590 A1 * | 3/2007 | Cosentino .......... | G01G 23/3735 |
| | | | 705/22 |
| 2016/0239637 A1 * | 8/2016 | Miller ..................... | G16H 40/67 |
| 2017/0017765 A1 * | 1/2017 | Yegge ................... | G16H 40/63 |

| | | | |
|---|---|---|---|
| 2018/0020093 A1 | 1/2018 | Bentitou et al. | |
| 2019/0069145 A1 * | 2/2019 | Dantsker ............... | G06F 40/169 |
| 2019/0114321 A1 * | 4/2019 | Lam ................... | G06F 16/24522 |
| 2019/0142062 A1 * | 5/2019 | Dayama ................... | A24F 47/00 |
| | | | 131/270 |
| 2020/0098384 A1 * | 3/2020 | Nematihosseinabadi ..................... | |
| | | | G10L 25/66 |
| 2020/0228470 A1 * | 7/2020 | Koo ........................ | G06Q 50/40 |
| 2020/0251198 A1 * | 8/2020 | Lavender ................. | G06N 5/01 |
| 2021/0064932 A1 * | 3/2021 | Wang .................. | G06F 16/9024 |
| 2021/0082548 A1 * | 3/2021 | Bloxton ................. | G16H 20/30 |
| 2021/0327582 A1 * | 10/2021 | Joshi ....................... | G16H 40/20 |
| 2022/0134119 A1 * | 5/2022 | McDonald ........... | A61N 1/0551 |
| | | | 607/46 |
| 2022/0229993 A1 * | 7/2022 | Vu .................... | G06V 30/19147 |
| 2022/0262495 A1 * | 8/2022 | Kanda .................... | G16H 20/60 |

(Continued)

*Primary Examiner* — Jason S Tiedeman
(74) *Attorney, Agent, or Firm* — ALLEN, DYER, DOPPELT, + GILCHRIST, P.A. Attorneys at Law

(57) ABSTRACT

A healthcare communications system may include a user interface device associated with a given patient in a healthcare facility and configured to listen for a voice activation command from the given patient. The healthcare communications system may also include a healthcare communications server configured to obtain medical history data associated with the given patient and determine a medical condition of the given patient based upon the medical history data. The healthcare communications server may also be configured to load an initial chatbot conversation script associated with the determined medical condition, and audibly operate a chatbot conversation with the given patient via the user interface device using the initial chatbot conversation script and based upon the voice activation command. The healthcare communications server may further be configured to generate and communicate a medical supply stocking list for the healthcare facility based upon the chatbot conversation and the determined medical condition.

18 Claims, 12 Drawing Sheets

(56) References Cited

U.S. PATENT DOCUMENTS

| | | | | |
|---|---|---|---|---|
| 2022/0338756 A1* | 10/2022 | Dzhekiev | ................ | G10L 25/66 |
| 2022/0353213 A1* | 11/2022 | Sharma | .................. | G06N 20/00 |
| 2023/0014078 A1* | 1/2023 | Kayser | ............ | G06Q 10/06311 |
| 2023/0110941 A1* | 4/2023 | Makhija | ................ | G06F 40/284 |
| | | | | 709/224 |
| 2023/0187031 A1* | 6/2023 | White | .................... | G10L 15/22 |
| | | | | 705/2 |
| 2023/0263393 A1* | 8/2023 | Ray | ....................... | A61B 5/1113 |
| | | | | 340/539.13 |
| 2024/0221909 A1* | 7/2024 | Palamadai | ............. | G16H 50/30 |
| 2024/0370902 A1* | 11/2024 | Miglani | ................. | G16H 40/00 |
| 2024/0412866 A1* | 12/2024 | Wen | ........................ | G16H 40/67 |
| 2025/0098960 A1* | 3/2025 | Neitzell | ................ | G06Q 30/04 |

\* cited by examiner

50

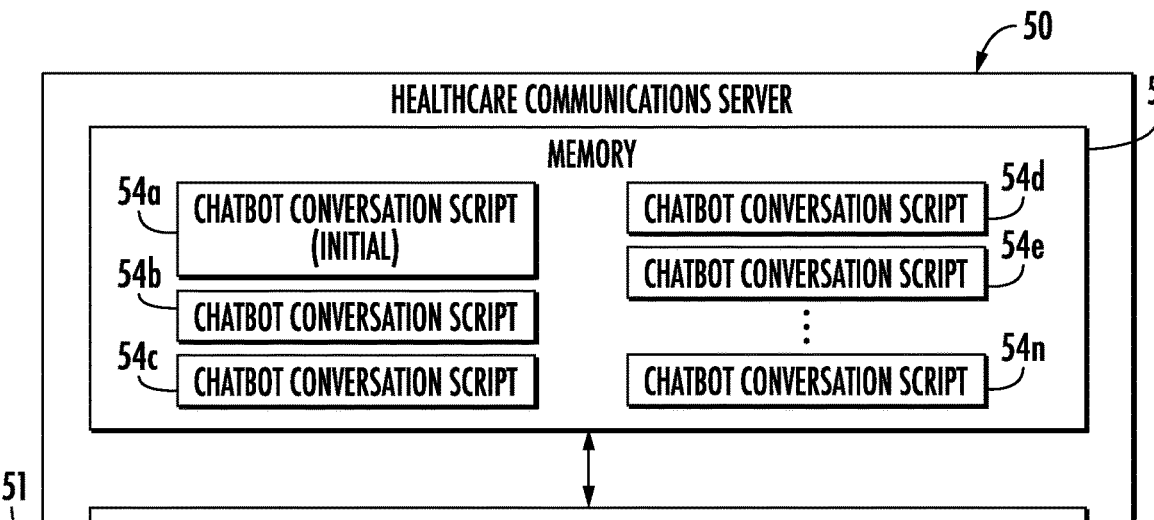

52

HEALTHCARE COMMUNICATIONS SERVER

MEMORY

54a CHATBOT CONVERSATION SCRIPT (INITIAL)

54b CHATBOT CONVERSATION SCRIPT

54c CHATBOT CONVERSATION SCRIPT

54d CHATBOT CONVERSATION SCRIPT

54e CHATBOT CONVERSATION SCRIPT

⋮

54n CHATBOT CONVERSATION SCRIPT

51

PROCESSOR

- OBTAIN MEDICATION HISTORY DATA ASSOCIATED WITH THE GIVEN PATIENT

- DETERMINE A MEDICAL CONDITION OF THE GIVEN PATIENT BASED UPON THE MEDICAL HISTORY DATA

- LOAD AN INITIAL CHATBOT CONVERSATION SCRIPT ASSOCIATED WITH THE DETERMINED MEDICAL CONDITION

- AUDIBLY OPERATE A CHATBOT CONVERSATION WITH THE GIVEN PATIENT VIA THE USER INTERFACE DEVICE USING THE INITIAL CHATBOT CONVERSATION SCRIPT AND BASED UPON THE VOICE ACTIVATION COMMAND (E.G., DURING OPERATION OF THE CHATBOT CONVERSATION, OBTAIN A PATIENT QUERY AND RESPOND TO THE PATIENT QUERY USING THE INITIAL CHATBOT CONVERSATION SCRIPT; DETERMINE WHETHER THE QUERY CANNOT BE RESPONDED TO USING THE INITIAL CHATBOT CONVERSATION SCRIPT, AND TRANSFER COMMUNICATIONS TO A REMOTE COMMUNICATIONS DEVICE ASSOCIATED WITH A HEALTHCARE PROVIDER)

- OPTIONALLY UPDATE THE INITIAL CHATBOT CONVERSATION SCRIPT WITH AN UPDATED CHATBOT CONVERSATION SCRIPT FROM CHATBOT CONVERSATION SCRIPTS BASED UPON THE CHATBOT CONVERSATION (E.G., OPERATE A MACHINE LEARNING ALGORITHM TO LEARN WHICH CHATBOT CONVERSATION SCRIPT FROM THE PLURALITY THEREOF TO LOAD AS THE UPDATED CHATBOT CONVERSATION SCRIPT BASED UPON DIFFERENT CHATBOT CONVERSATIONS WITH DIFFERENT PATIENTS; POLL THE CHATBOT CONVERSATION FOR KEYWORDS EACH ASSOCIATED WITH A GIVEN UPDATED CHATBOT CONVERSATION SCRIPT, AND LOAD THE GIVEN UPDATED CHATBOT CONVERSATION SCRIPT BASED UPON THE KEYWORDS).

- GENERATE AND COMMUNICATE A MEDICAL SUPPLY STOCKING LIST FOR THE HEALTHCARE FACILITY BASED UPON THE CHATBOT CONVERSATION AND THE DETERMINED MEDICAL CONDITION

- OPTIONALLY GENERATE AND COMMUNICATE STAFFING LEVELS FOR THE HEALTHCARE FACILITY BASED UPON THE CHATBOT CONVERSATION

*FIG. 3*

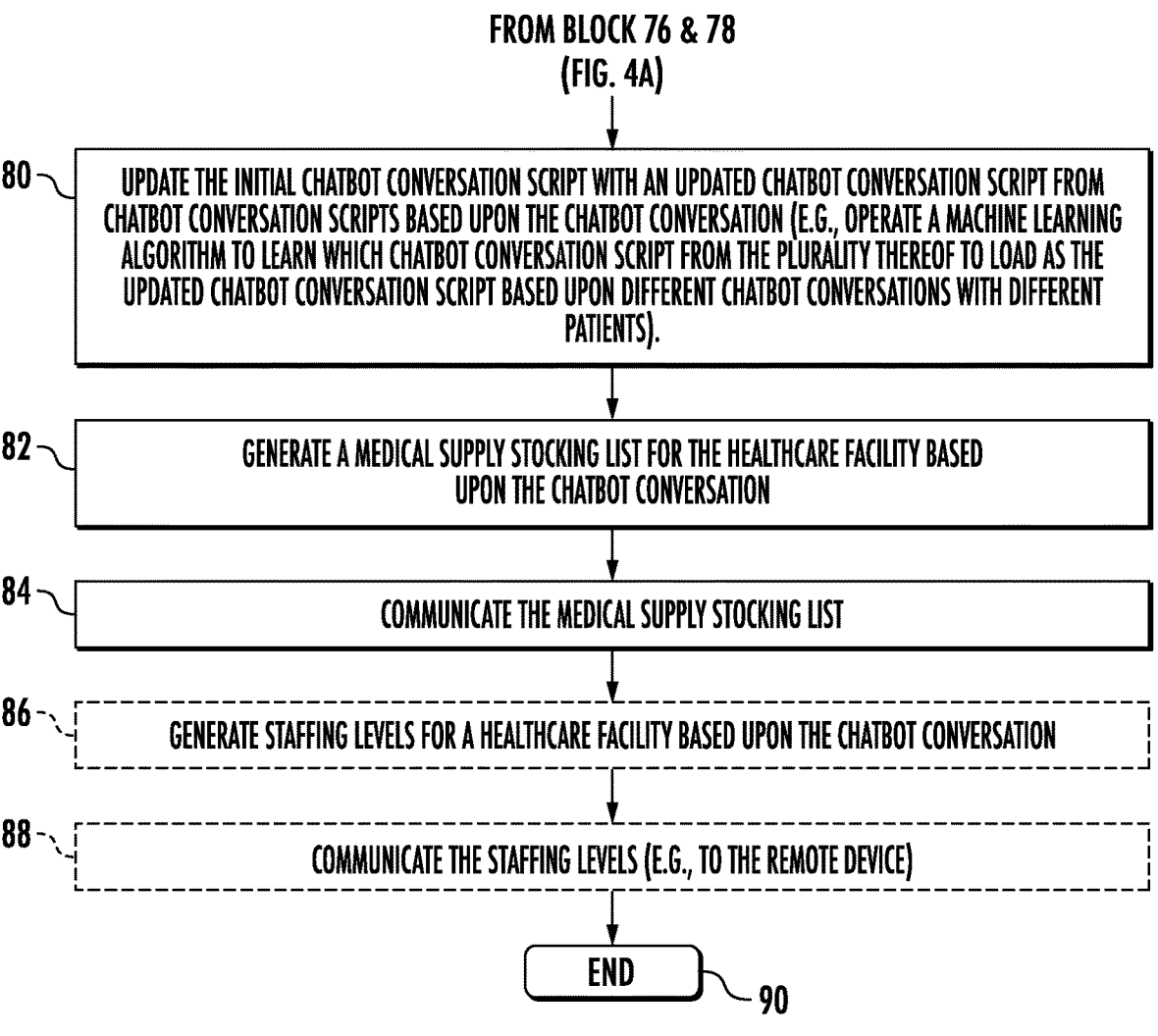

FROM BLOCK 76 & 78
(FIG. 4A)

80 — UPDATE THE INITIAL CHATBOT CONVERSATION SCRIPT WITH AN UPDATED CHATBOT CONVERSATION SCRIPT FROM CHATBOT CONVERSATION SCRIPTS BASED UPON THE CHATBOT CONVERSATION (E.G., OPERATE A MACHINE LEARNING ALGORITHM TO LEARN WHICH CHATBOT CONVERSATION SCRIPT FROM THE PLURALITY THEREOF TO LOAD AS THE UPDATED CHATBOT CONVERSATION SCRIPT BASED UPON DIFFERENT CHATBOT CONVERSATIONS WITH DIFFERENT PATIENTS).

82 — GENERATE A MEDICAL SUPPLY STOCKING LIST FOR THE HEALTHCARE FACILITY BASED UPON THE CHATBOT CONVERSATION

84 — COMMUNICATE THE MEDICAL SUPPLY STOCKING LIST

86 — GENERATE STAFFING LEVELS FOR A HEALTHCARE FACILITY BASED UPON THE CHATBOT CONVERSATION

88 — COMMUNICATE THE STAFFING LEVELS (E.G., TO THE REMOTE DEVICE)

END — 90

FIG. 4B

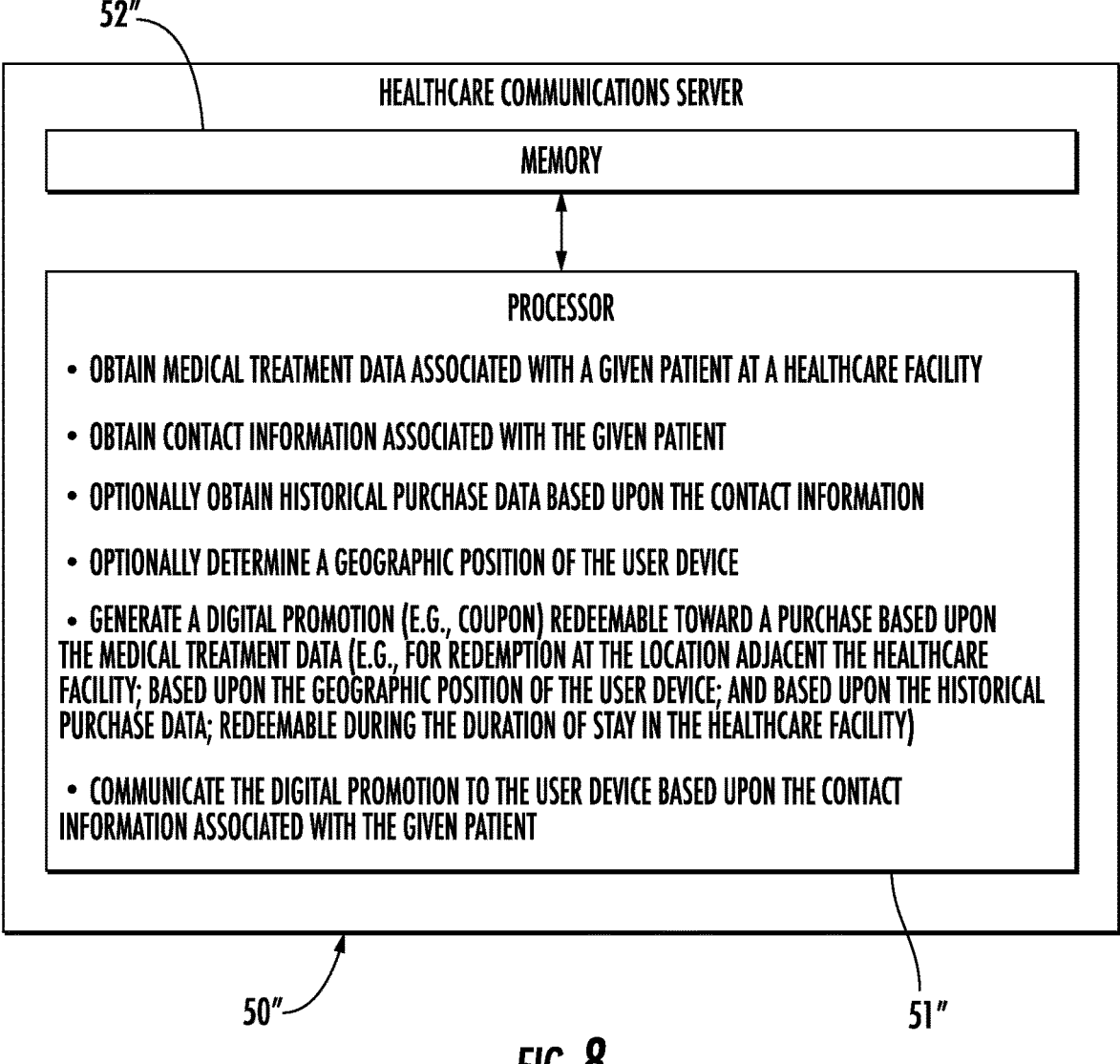

52″

HEALTHCARE COMMUNICATIONS SERVER

MEMORY

PROCESSOR

• OBTAIN MEDICAL TREATMENT DATA ASSOCIATED WITH A GIVEN PATIENT AT A HEALTHCARE FACILITY

• OBTAIN CONTACT INFORMATION ASSOCIATED WITH THE GIVEN PATIENT

• OPTIONALLY OBTAIN HISTORICAL PURCHASE DATA BASED UPON THE CONTACT INFORMATION

• OPTIONALLY DETERMINE A GEOGRAPHIC POSITION OF THE USER DEVICE

• GENERATE A DIGITAL PROMOTION (E.G., COUPON) REDEEMABLE TOWARD A PURCHASE BASED UPON THE MEDICAL TREATMENT DATA (E.G., FOR REDEMPTION AT THE LOCATION ADJACENT THE HEALTHCARE FACILITY; BASED UPON THE GEOGRAPHIC POSITION OF THE USER DEVICE; AND BASED UPON THE HISTORICAL PURCHASE DATA; REDEEMABLE DURING THE DURATION OF STAY IN THE HEALTHCARE FACILITY)

• COMMUNICATE THE DIGITAL PROMOTION TO THE USER DEVICE BASED UPON THE CONTACT INFORMATION ASSOCIATED WITH THE GIVEN PATIENT

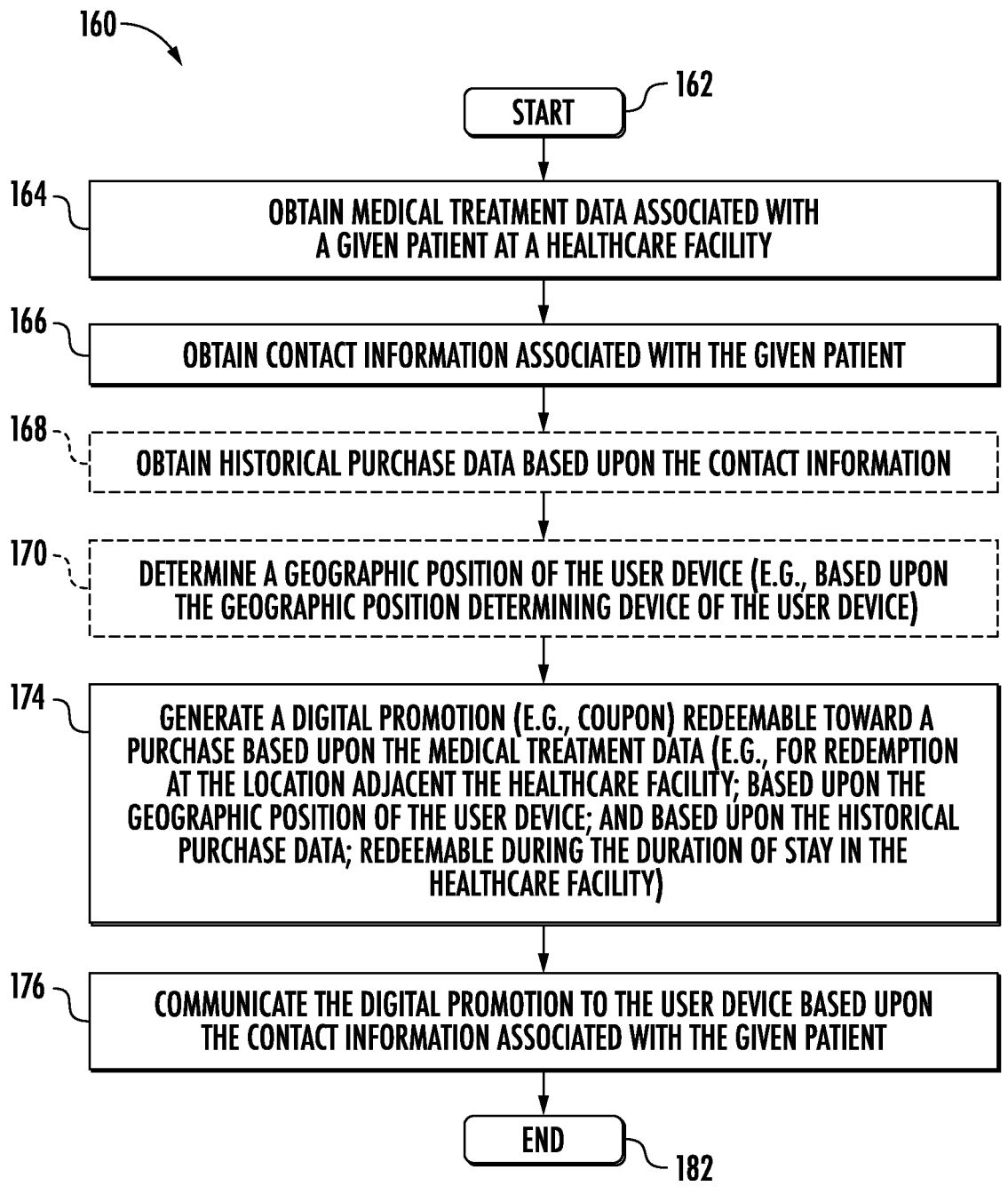

160

162
START

164
OBTAIN MEDICAL TREATMENT DATA ASSOCIATED WITH
A GIVEN PATIENT AT A HEALTHCARE FACILITY

166
OBTAIN CONTACT INFORMATION ASSOCIATED WITH THE GIVEN PATIENT

168
OBTAIN HISTORICAL PURCHASE DATA BASED UPON THE CONTACT INFORMATION

170
DETERMINE A GEOGRAPHIC POSITION OF THE USER DEVICE (E.G., BASED UPON
THE GEOGRAPHIC POSITION DETERMINING DEVICE OF THE USER DEVICE)

174
GENERATE A DIGITAL PROMOTION (E.G., COUPON) REDEEMABLE TOWARD A
PURCHASE BASED UPON THE MEDICAL TREATMENT DATA (E.G., FOR REDEMPTION
AT THE LOCATION ADJACENT THE HEALTHCARE FACILITY; BASED UPON THE
GEOGRAPHIC POSITION OF THE USER DEVICE; AND BASED UPON THE HISTORICAL
PURCHASE DATA; REDEEMABLE DURING THE DURATION OF STAY IN THE
HEALTHCARE FACILITY)

176
COMMUNICATE THE DIGITAL PROMOTION TO THE USER DEVICE BASED UPON
THE CONTACT INFORMATION ASSOCIATED WITH THE GIVEN PATIENT

END
182

FIG. 9

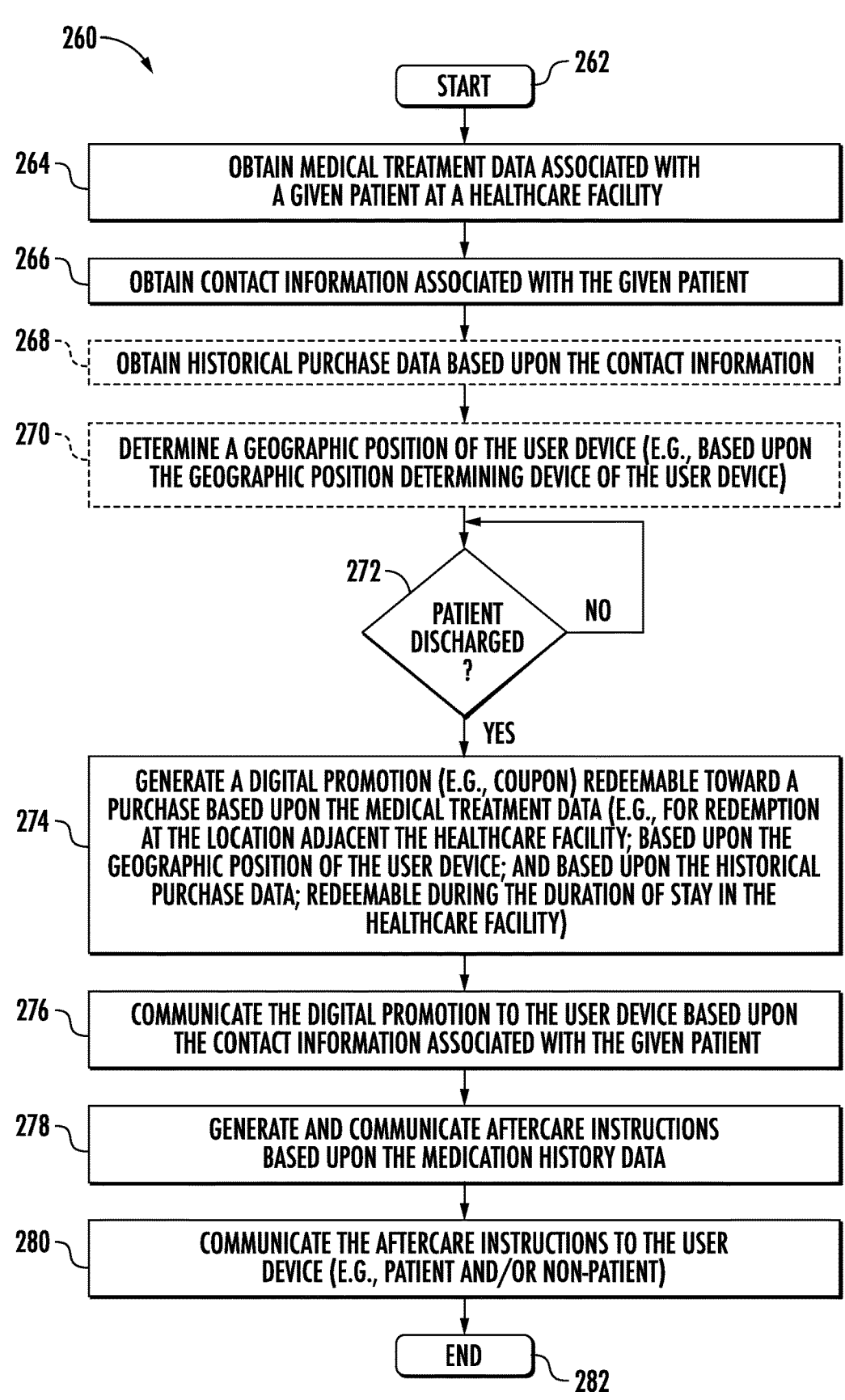

260

262
START

264
OBTAIN MEDICAL TREATMENT DATA ASSOCIATED WITH
A GIVEN PATIENT AT A HEALTHCARE FACILITY

266
OBTAIN CONTACT INFORMATION ASSOCIATED WITH THE GIVEN PATIENT

268
OBTAIN HISTORICAL PURCHASE DATA BASED UPON THE CONTACT INFORMATION

270
DETERMINE A GEOGRAPHIC POSITION OF THE USER DEVICE (E.G., BASED UPON
THE GEOGRAPHIC POSITION DETERMINING DEVICE OF THE USER DEVICE)

272
PATIENT
DISCHARGED
?
NO

YES

274
GENERATE A DIGITAL PROMOTION (E.G., COUPON) REDEEMABLE TOWARD A
PURCHASE BASED UPON THE MEDICAL TREATMENT DATA (E.G., FOR REDEMPTION
AT THE LOCATION ADJACENT THE HEALTHCARE FACILITY; BASED UPON THE
GEOGRAPHIC POSITION OF THE USER DEVICE; AND BASED UPON THE HISTORICAL
PURCHASE DATA; REDEEMABLE DURING THE DURATION OF STAY IN THE
HEALTHCARE FACILITY)

276
COMMUNICATE THE DIGITAL PROMOTION TO THE USER DEVICE BASED UPON
THE CONTACT INFORMATION ASSOCIATED WITH THE GIVEN PATIENT

278
GENERATE AND COMMUNICATE AFTERCARE INSTRUCTIONS
BASED UPON THE MEDICATION HISTORY DATA

280
COMMUNICATE THE AFTERCARE INSTRUCTIONS TO THE USER
DEVICE (E.G., PATIENT AND/OR NON-PATIENT)

END
282

FIG. 11

HEALTHCARE COMMUNICATIONS SYSTEM GENERATING CHATBOT CONVERSATION BASED MEDICAL SUPPLY STOCKING LIST AND RELATED METHODS

TECHNICAL FIELD

The present invention relates to the field of healthcare, and, more particularly, to healthcare communications and related methods.

BACKGROUND

A healthcare facility may provide one or more healthcare services, for example. An exemplary healthcare facility may include a hospital, nursing home, rehabilitation facility, or other centralized location where healthcare services may be provided.

A typical healthcare facility, such as, for example, a hospital includes one or more wards that house hospital beds for patients. The wards or departments may include an emergency department, intensive care unit, long term care unit, etc. The departments may be organized by injury or sickness, or by affected body parts.

Each ward of a healthcare facility or hospital may have a team of healthcare providers. For example, the healthcare providers may include doctors, nurses, nursing assistants, technicians, and orderlies. Each healthcare provider may perform one or more functions, for example, serving food, administering medications, taking vitals, etc.

SUMMARY

A healthcare communications system may include a user interface device associated with a given patient in a healthcare facility and configured to listen for a voice activation command from the given patient. The healthcare communications system may also include a healthcare communications server configured to obtain medical history data associated with the given patient and determine a medical condition of the given patient based upon the medical history data. The healthcare communications server may also be configured to load an initial chatbot conversation script associated with the determined medical condition, and audibly operate a chatbot conversation with the given patient via the user interface device using the initial chatbot conversation script and based upon the voice activation command. The healthcare communications server may further be configured to generate and communicate a medical supply stocking list for the healthcare facility based upon the chatbot conversation and the determined medical condition.

The healthcare communications server may be configured to, during operation of the chatbot conversation, obtain a patient query and respond to the patient query based upon the initial chatbot conversation script. The healthcare communications server may be configured to determine, during the chatbot conversation, that the patient query cannot be responded to using the initial chatbot conversation script, and transfer communications to a remote communications device associated with a healthcare provider, for example.

The healthcare communications server may be configured to update the initial chatbot conversation script with an updated chatbot conversation script from a plurality of chatbot conversation scripts based upon the chatbot conversation. The healthcare communications server may be configured to operate a machine learning algorithm to learn which chatbot conversation script from the plurality thereof to load as the updated chatbot conversation script based upon a plurality of different chatbot conversations with a plurality of different patients, for example. The healthcare communications server may be configured to generate and communicate staffing levels for the healthcare facility based upon the chatbot conversation, for example.

The healthcare communications system may further include a meal request interface device, and the healthcare communications server may be configured to generate and communicate a meal order to the meal request interface device based upon the chatbot conversation, and provide a meal order status update within the chatbot conversation. The healthcare communications server may be configured to poll the chatbot conversation for keywords each associated with a given updated chatbot conversation script, and load the given updated chatbot conversation script based upon the keywords, for example.

A method aspect is directed to a method of healthcare communications. The method may include using a healthcare communications server to obtain medical history data associated with a given patient, and determine a medical condition of the given patient based upon the medical history data. The method may also include using the healthcare communications server to load an initial chatbot conversation script associated with the determined medical condition, and audibly operate a chatbot conversation with the given patient via a user interface device using the initial chatbot conversation script and based upon a voice activation command. The user interface device may be associated with the given patient in a healthcare facility and configured to listen for the voice activation command from the given patient. The method may further include using the healthcare communications server to generate and communicate a medical supply stocking list for the healthcare facility based upon the chatbot conversation and the determined medical condition.

A computer readable medium aspect is directed to non-transitory computer readable medium for healthcare communications. The non-transitory computer readable medium includes computer executable instructions that when executed by a processor cause the processor to perform operations that may include obtaining medical history data associated with a given patient, and determining a medical condition of the given patient based upon the medical history data. The operations may also include loading an initial chatbot conversation script associated with the determined medical condition, and audibly operating a chatbot conversation with the given patient via a user interface device using the initial chatbot conversation script and based upon a voice activation command. The user interface device may be associated with the given patient in a healthcare facility and configured to listen for the voice activation command from the given patient. The operations may further include generating and communicating a medical supply stocking list for the healthcare facility based upon the chatbot conversation and the determined medical condition.

BRIEF DESCRIPTION OF THE DRAWINGS

FIG. 3 is a schematic block diagram of the healthcare communications server of the healthcare communications system of FIG. 1.

FIGS. 4A and 4B are flow diagrams of operation of the healthcare communications server of FIG. 3.

FIG. 8 is a block diagram of the healthcare communications server of the healthcare communications system of FIG. 6.

FIG. 9 is a flow diagram of operation of the healthcare communications server of FIG. 8.

FIG. 11 is a flow diagram of operation of the healthcare communications server of FIG. 10.

DETAILED DESCRIPTION

The present invention will now be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout, and prime and multiple prime notation is used to indicate similar elements in alternative embodiments.

Figure 1:
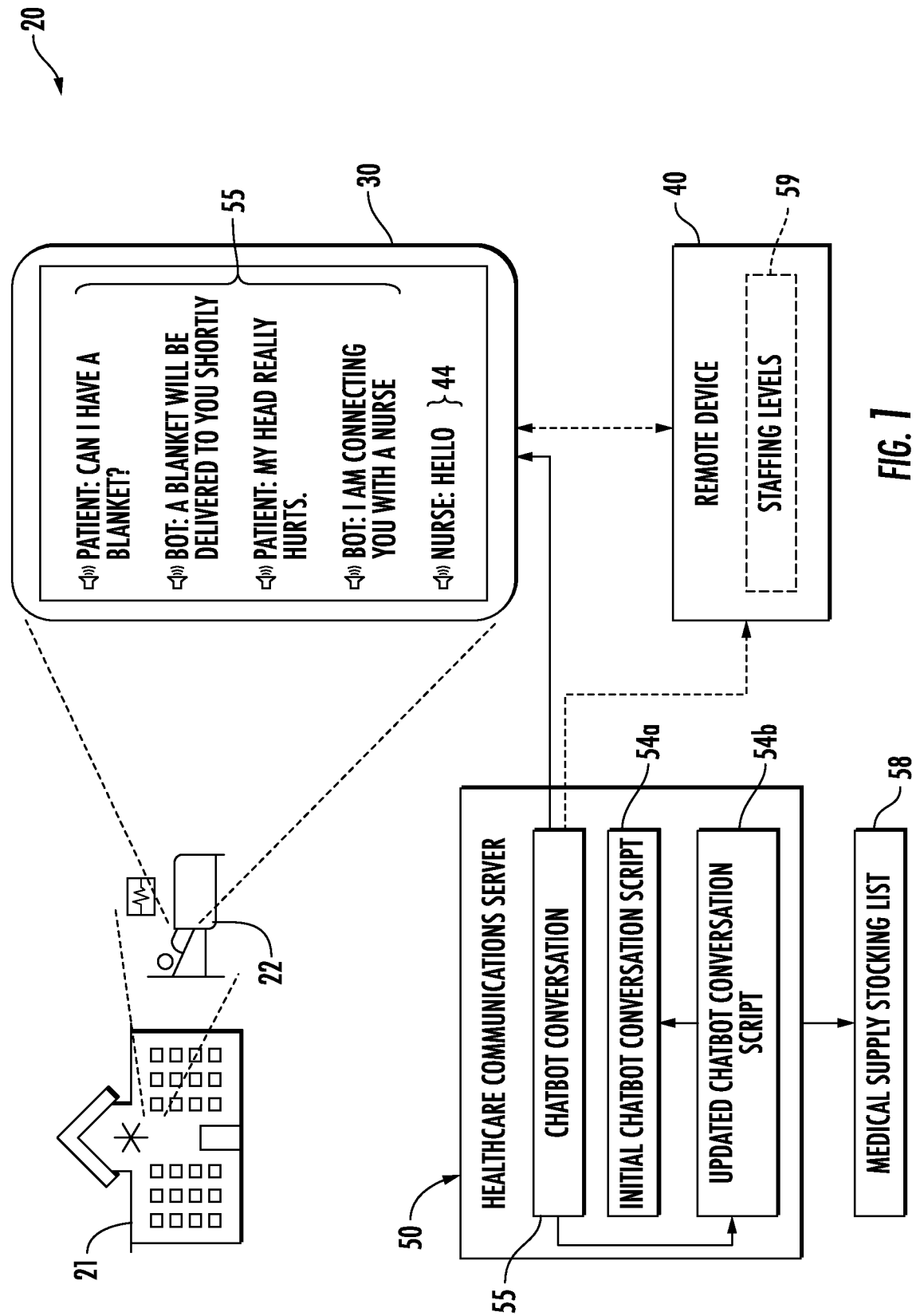
FIG. 1 is a schematic diagram of a healthcare communications system in accordance with an embodiment.
Figure 2:
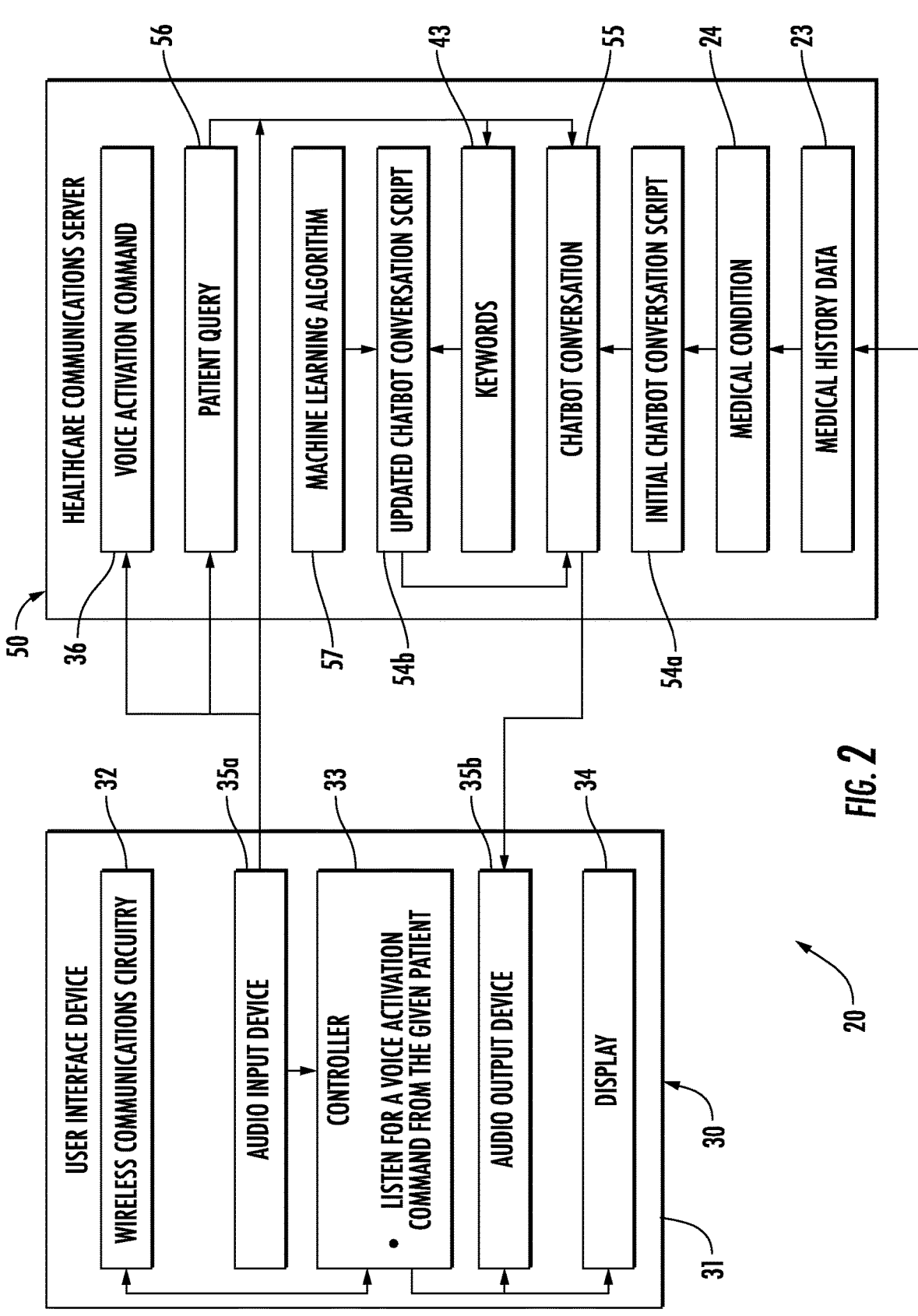
FIG. 2 is a schematic operational block diagram of a portion of the healthcare communications system of FIG. 1.

Referring initially to FIGS. 1-3, a healthcare communications system 20 includes a user interface device 30. The user interface device 30 is associated with a given patient 22 in a healthcare facility 21. The user interface device 30 is illustratively in the form of a mobile wireless communications device, and more particularly, a tablet computer. The user interface device 30 may be in the form of another type of device, for example, a mobile phone or smartphone, a virtual assistant device, a laptop computer, or a smart television, for example. The user interface device 30 may be a wired or wireless user interface device, for example. Those skilled in the art will appreciate that while the user interface device 30 may be in the form of a virtual assistant device, any of the above devices, such as a tablet computer or smart phone, may operate a virtual assistant application, or execute virtual assistant functions.

The user interface device 30, as a tablet computer, illustratively includes a housing 31, wireless communications circuitry 32 (e.g., cellular, Wifi, Bluetooth, and/or other long- and/or short-range communications circuitry) carried by the housing and coupled to a controller 33, and a display 34 also carried by the housing and coupled to the controller. The display 34 may be in the form of a touch-screen display that may accept input thereto from a user in addition to providing a display. An audio input device 35a and an audio output device 35b are also carried by the housing 31 and coupled to the controller 33.

The user interface device 30 is configured to listen for a voice activation command 36 from the given patient 22. More particularly, the user interface device 30 polls for input to the audio input device 35a and applies speech recognition to determine whether the speech activation command has been received. An exemplary voice activation command may include "Hey Nurse", for example. The controller 33 may perform the speech recognition or communicate the obtained speech or voice data to a server for processing.

Exemplary techniques for speech recognition or to identify the voice activation command 36 will now be described.

According to an embodiment, the user interface device 30 via the audio input device 35a and controller 33 may apply an acoustic model whereby raw soundwave data obtained from the audio input device is translated, via the controller, into phonemes, which are any of the perceptually distinct units of sound in a specified language that distinguish one word from another. The phonemes may be joined together based upon a language model to form words, and the phonemes may be joined together based upon spoken variations (e.g., age, dialect, accent, etc.).

An n-gram model may be used that uses, for example, the previous n-words as context to identify a given word. A higher n-number may correspond to increased accuracy, but oftentimes involves longer processing times. Another model or algorithm may include the Hidden Markov Model (HMM). Unlike the n-gram model, the HMM model uses words in front of a given word and without knowledge of the previous words. Stated alternatively, the HMM model or algorithm looks forward instead of backward in terms of context words. The HMM algorithm applies probabilistic statistics to make an educated guess as to the next words. The HMM algorithm uses other information about a target word, such as metadata (e.g., noun, verb, adjective, etc.).

Another speech recognition technique may use deep learning to create an end-to-end model that may be more accurate, quicker, and easier to deploy on mobile wireless communications devices, such as, for example, smart phones with a virtual assistant or virtual assistant devices. The end-to-end model may implement an artificial neural network which may conceptually be considered a many-layered, or deep, architecture. Nodes are assigned weights, and when the neural network is active, a node receives different data over its connections. The data is weighted, and the resulting weighted data is added to yield a number. If the number is below a threshold value, the node passes no data to the next layer, while if the number is above the threshold value, the number is sent or communicated from the node's outgoing connections.

As will be appreciated by those skilled in the art, particularly advantageous algorithms for processing speech may be referred to as a recurrent neural network (RNN). RNN algorithms may be particularly suited for sequential data, such as, for example, speech since they have knowledge of the previous data such that the previous output is used as an input. Since many words are part of a sentence, knowledge of the words that were previously processed and using that information to generate a next prediction may increase accuracy with respect to speech recognition.

Yet another algorithm may be particularly advantageous with respect to training speech recognition models. A machine learning algorithm learns based upon repeated data input. A classifier may accept as input audio (i.e., training audio) and a corresponding truth audio. However, the correspondence of the words in the audio and the transcript may be subject to alignment issues. To address alignment issues, a connectionist temporal classification (CTC) may be used. The CTC algorithm uses a probabilistic approach to align the transcripts with the training data audio. How exactly this works is beyond the scope of this article, but suffice to say that this is a key ingredient for training a neural network to perform speech recognition tasks.

The healthcare communications system 20 also includes a healthcare communications server 50. The healthcare communications server 50 includes a processor 51 and an associated memory 52. While operations of the healthcare communications server 50 are described herein, those skilled in the art will appreciate that the processor 51 and the memory 52 cooperate to perform the operations.

Figure 4A:
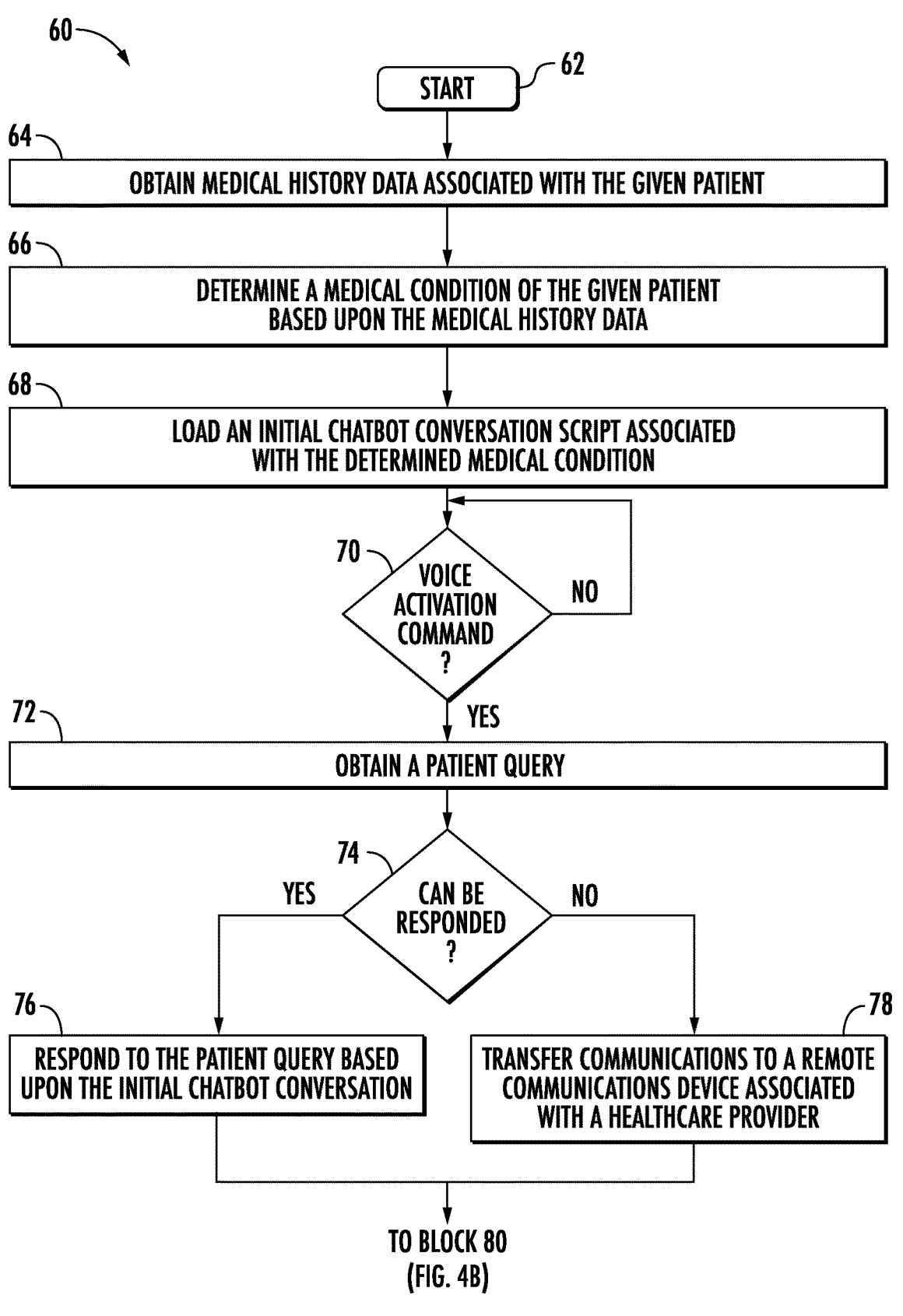

Referring now to the flowchart 60 in FIGS. 4A-4B, beginning at Block 62, operation of the healthcare communications server 50 will now be described. At Block 64, the healthcare communications server 50 obtains medical history data 23 associated with the given patient 22. The medical history data 23 may include medical images, medical codes, written physician observations, medications, biometrics of the given patient 22, patient hospitalizations, current healthcare facility location, etc. The healthcare communications server 50 may communicate with one or more medical data or medical records servers to obtain the data based upon, for example, a unique patient identifier associated with the given patient 22. In other words, the unique patient identifier may be used as an index to retrieve the medical history data 23 for the given patient 22.

The healthcare communications server 50, at Block 66, determines a medical condition 24 of the given patient 22 based upon the medical history data 23. The healthcare communications server 50 may determine the medical condition 24 based upon keywords in the medical history data 23 corresponding to a given medical condition. The healthcare communications server 50 may catalog terms in documents and document types to determine a given medication condition 24. For example, the healthcare communications server 50 may determine that the given patient 22 has a broken arm 24 based upon certain terms in the medical history data 23, such as, "fracture", "arm", and "cast", and the existence of x-rays in the medical history data. The healthcare communications server 50 may also operate a machine learning algorithm that accepts as input or training data the medical history data 23 (e.g., written words, phrases, and medical document types) for a given patient 22 and outputs the determined medical condition 24. As data is added to the given patient's medical files, and thus the medical history data 23, the machine learning algorithm may be updated or trained, and another output generated. In some embodiments, the medical history data of other patients may be used or provided as input to the machine learning algorithm to generate or determine the medical condition 24 for the given patient. As medical history data 23 is updated, for example, as new medical history data is added, the machine learning algorithm may be executed to determine the medical condition 24.

The healthcare communications server 50 loads an initial chatbot conversation script 54a associated with the determined medical condition 24 (Block 68). The healthcare communications server 50 may store, for example, in the memory 52 different chatbot conversation scripts 54a-54n each corresponding to a different medical condition 24. For example, with respect to the broken arm medical condition, the initial chatbot conversation script 54a may correspond to the broken arm condition, while for a patient determined to have renal issues, the healthcare communications server 50 loads the initial chatbot conversation script 54a corresponding to renal failure, for example.

The healthcare communications server 50 audibly operates a chatbot conversation 55 with the given patient 22 using the initial chatbot conversation script 54a and based upon the voice activation command 36. More particularly, the healthcare communications server 50 cooperates with the user interface device 30 to determine when the voice activation command 36 has been audibly spoken by the given patient 22 (Block 70). If at Block 70, the voice activation command 36 has been received, the healthcare communications server 50 initiates an audible chatbot conversation 55 with the given patient using the initial chatbot conversation script 54a. As will be appreciated by those skilled in the art, a given patient with a given medical condition may have different needs or desires. For example, a broken bone patient that may have just had surgery may be experiencing relatively high levels of pain. Thus, the given patient 22 may be desirous of pain medication. However, some pain medications may make the given patient 22 feel cold, and thus, the given patient may request a blanket. Accordingly, the initial chatbot conversation script 54a for a given patient 22 having a surgically repaired broken bone 24 may have questions or be prepared to answer questions such as, for example, "I am cold", "Can I have a blanket?", "I feel a lot of pain", and "Can I have some pain medication?"

In other words, during operation of the chatbot conversation 55, the healthcare communications server 55 may obtain a patient query 56 (Block 72) (e.g., along the lines noted above) and, using the initial chatbot conversation script 54a as conversational guide, respond to the patient query 56 (Block 76). An exemplary audible response may include, "A blanket will be delivered to you shortly," "I have adjusted the room temperature to be warmer", or "I have ordered you a pain medication".

The healthcare communications server 50 may optionally, respond to the patient query 56 by also generating and communicating a request to the appropriate person (nurse, aid, etc.) or department for the request. For example, the healthcare communications server 50 may route a request to a device, for example, mobile device, associated with a healthcare professional (e.g., nurse, doctor, nursing assistant, etc.) corresponding to the request. In other words, a request for a blanket may be generated and communicated to a device associated with an assistant, while a request for more medication may be communicated to a nurse or doctor. In some embodiments, the healthcare communications server 50 may operate controllable devices, for example, internet-of-things (IoT) devices, at the healthcare facility 21 using the appropriate communications protocols. The healthcare communications server 50 may operate IoT thermostats, light switches, etc.

The healthcare communications server 50 may determine, during the chatbot conversation 55 that the patient query 56 cannot be responded to using the initial chatbot conversation script 54a (Block 74). More particularly, if the patient query 56 is not one that has a response using the initial chatbot conversation script 54a or can be learned determined using artificial intelligence (AI) techniques, as will be described in further detail below. If, at Block 74, the patient query 56 can be responded to using the initial chatbot conversation script 54a, the healthcare communications server 50 responds to the patient query, as described above (Block 76). If the healthcare communications server 50 cannot respond to the patient query 56 using the initial chatbot conversation script 54a (Block 74), the healthcare communications server may transfer the communications to a remote communications device 40 associated with a healthcare provider (Block 78), for example, for establishing a live communication 44 with the healthcare provider. Upon or after communications have been transferred to the remote device 40, the healthcare communications server 50 may update the initial chatbot conversation script 54a, at Block 80, as will be described in further detail below. Alternatively, operations may end at Block 90.

Similarly, to the healthcare communications server 50 generating and communicating a request to a healthcare provider based upon the patient query 56, the healthcare communications server may initiate communications with the remote communications device 40, for example, using internet telephony technologies or voice-over-internet protocol (VOIP). Upon connection with the remote communications device 40, the healthcare communications server 50 may connect to or act as a bridge between the user interface device 30 and the remote communications device so that the given patient can audibly or verbally communicate, live, with the healthcare provider. The healthcare communications server 50 may, in cases where the patient query 56 cannot be responded to using the initial chatbot conversation script 54a, audibly respond to the patient query with a prompt for the given patient to standby while "we connect you with the appropriate healthcare provider." Of course, other and/or additional responses may be provided. In some embodiments, the healthcare communications server 50 may connect the given patient, based upon the patient query 56, to a personal contact that may not be a healthcare provider associated with the healthcare facility 21. For example, the healthcare communications server 50 may, during operation of the chatbot conversation 55, transfer communications to a remote device associated with a family member or other listed contact, for example, using the medical history data 23 to obtain a telephone number or other identifier to establish and transfer verbal communication, as will be appreciated by those skilled in the art. Further details of obtaining and using contact information associated with the given patient 22 are described below.

At Block 80, the healthcare communications server 50 updates the initial chatbot conversation script 54a with an updated chatbot conversation script 54b from among updated chatbot conversation scripts 54b-54n based upon the chatbot conversation 55. The healthcare communications server 50 may determine which chatbot conversation script 54b-54n to select when the patient query cannot be responded to, or when a threshold amount of keywords 43 associated with the initial (or subsequent) chatbot conversation script 54a is exceeded. Exceeding a keyword threshold may be indicative that the current chatbot conversation script 54a-54n may no longer be suitable for the given chatbot conversation 55. Of course, other and/or additional techniques may be used to determine when to change the chatbot conversation script 54a-54n, for example, based upon a machine learning algorithm 57. Further details of how keywords 43 and the machine learning algorithm 57 are used as they relate to the chatbot conversation scripts 54a-54n will be described in further detail below.

The healthcare communications server 50 may update the initial chatbot conversation 54a based upon a machine learning algorithm 57. More particularly, the healthcare communications server 50 may operate the machine learning algorithm 57 to learn which chatbot conversation script 54a-54n from among the chatbot conversation scripts based upon different chatbot conversations with different patients. The existing chatbot conversation scripts 54a-54n may be input to the machine learning algorithm 57. The machine learning algorithm 57 may be considered a deep learning or artificial intelligence (AI) based algorithm that employs or uses neural networks as a basis for operation, as will be described in further detail below.

As chatbot conversations from the given patient 22 and other patients occur, they too are input into the machine learning algorithm 57. The chatbot conversations 55 may be paired in the form of message-response or query-response pairs that are input to a classifier. Identification of the query-response pairs may be determined based upon rules, for example, timing between a query and associated response. By pairing the queries and responses, the healthcare communications server 50 may classify one conversation or given patient as the response in a conversation, and the incoming dialogue is further used as textual indicators that can help predict the response. The healthcare communications server 50 may perform pre-processing to further understand variations in audible or spoken queries. The healthcare communications server 50 may thus learn by tokenizing, stemming, and lemmatizing the chatbot conversations, for example, applying a natural language toolkit (NTLK). The healthcare communications server 50 may create parse trees of the chatbot conversations for use as a reference.

The healthcare communications server 50 may operate the machine learning algorithm 57 in the operation of the chatbot conversation as being retrieval-based model. Indeed, as described herein, the chatbot conversation 55 operates based upon the chatbot conversation scripts 54a-54n, which may each be considered a repository of responses that it uses to address queries. The retrieval model advantageously has a higher accuracy rate compared to other models since it is based upon the retrieval of data (i.e., the chatbot conversation scripts 54a-54n). Since the chatbot conversation is audible, application of word vectors may be undesirable.

In an embodiment, the healthcare communications server 50 may, alternatively or additionally, poll the chatbot conversation 55 for keywords 43 each associated with a given updated chatbot conversation script 54b-54n. The keywords may be input to the machine learning algorithm 57, as described above, for example, to the classifier. The healthcare communications server 50 may count the keywords and conceptually place them in bins or histograms each representing an updated chatbot conversation script 54b-54n. After a threshold number of keywords 43 have been placed in a given bin, or associated with a corresponding updated chatbot conversation script 54b-54n, the healthcare communications server 50 may select and load that particular updated chatbot conversation script 54b-54n. In some embodiments, certain keywords 43 may be weighted such that the existence of these keywords may be considered to be two or more times another keyword. Of course, the healthcare communications server 50 may load the updated chatbot conversation script 54b-54n based upon one or more of the techniques described herein, or other techniques, as will be appreciated by those skilled in the art.

The healthcare communications server 50 may determine that an updated chatbot conversation script 54b-54n is desirable when the patient query 56 cannot be responded to, for example, using the initial chatbot conversation script 54. The transferring of communications to the remote communications device 40 associated with the healthcare provider may occur in addition to updating the initial chatbot conversation script 54a or as an alternative thereto. Alternatively, or additionally, the healthcare communications server 50 may update the initial chatbot conversation script 54a with an updated chatbot conversation script 54b-54n after obtaining updated medical history data 23 and/or after completion of the patient request or responding to the patient query 56. In other words, the healthcare communications server 50 may, via the chatbot conversation 55, change prompts and scripts based upon the interactions of the given patient during the chatbot conversation.

The healthcare communications server 50 may not update the initial chatbot conversation script 54a after each patient request and associated response, for example. The healthcare communications server 50 may determine a relevancy of the initial chatbot conversation script 54a and update the
initial chatbot conversation script with an updated chatbot
conversation script 54b-54n based upon one or more patient
queries 56. For example, if the chatbot conversation 55
changes such that the prompts, requests, and responses may
not be associated or aligned, the healthcare communications
server 50 may update the initial chatbot conversation script
54a with an updated chatbot conversation script 54b-54n.
The decision of when to update the initial chatbot conver-
sation script 54a may be made by the healthcare communi-
cations server 50 based upon the machine learning algorithm
and/or an amount of keywords 43, as described above. For
example, if keywords 43 more closely match or are associ-
ated with another chatbot conversation script 54b-54n than
the initial chatbot conversation script 54a, then the health-
care communications server 50 may update the initial chat-
bot conversation script. Of course, those skilled in the art
will appreciate that the healthcare communications server 50
may determine when to update any given chatbot commu-
nications script 54a-54n with an updated chatbot conversa-
tion script based upon other and/or additional criteria and
timing, e.g., on an ongoing basis. In other words, the
healthcare communications server 50 may update subse-
quent chatbot conversation scripts 54b-54n beyond the ini-
tial chatbot conversation script 54a. In some embodiments,
the healthcare communications server 50 may update also
upon the initial (or current) chatbot conversation script 54a
being unable to respond to the patient query 56.

The healthcare communications server 50 may generate a
medical supply stocking list 58 for the healthcare facility 21
based upon the chatbot conversation 55 and the determined
medical condition 24 (Block 82). The medical supply stock-
ing list may include quantities and descriptions of patient
comfort items, such as, for example, blankets, socks, etc., as
may be determined based upon the chatbot conversations 55.
More particularly, the healthcare communications server 50
may determine based upon patient queries 56 for a given
item, such as a blanket, that a given floor or ward may be low
in stock (e.g., based upon the number of requests for that
item), and that upon the next stocking, a certain number of
items should be stocked. Currently, many items are stocked
to a given ward or floor in a static fashion—that is, for
example, a fixed number in a given time frame (e.g., 5
blankets daily). The healthcare communications server 50
may advantageously provide a more accurate stocking. The
healthcare communications server 50 may provide the medi-
cal supply stocking list 58 for other and/or additional items,
such as tissues, water, medications or medicines, etc.

The healthcare communications server 50 may learn, or
use a machine learning algorithm to predict, based upon the
chatbot conversation 55 and the determined medical condi-
tion as input to the machine learning algorithm 57, when
certain medical supplies may be in further demand. The
healthcare communications server 50, at Block 84, commu-
nicates the medical supply stocking list 58 to the remote
communications device 40 or other remote device associated
with the healthcare facility 21.

At Block 86, the healthcare communications server 50
may optionally generate staffing levels 59 for the healthcare
facility 21 based upon the chatbot conversation 55. For
example, an increased number of requests or patient queries
56 may correspond to increased response times or delays for
servicing patient requests. However, by generating staffing
levels, times and dates when requests are increased can be
met with the appropriate staffing levels 59. The healthcare
communications server 50 may operate a machine learning
algorithm to learn correlations between a chatbot conversation 55, for example, patient queries 56, and determine an
appropriate staffing level (e.g., predict staffing levels 59
based upon the chatbot conversations). At Block 88, the
healthcare communications server 50 communicates the
staffing levels 59 to the remote communications device 40 or
other remote device associated with the healthcare facility
21. Operations end at Block 90.

Figure 5:
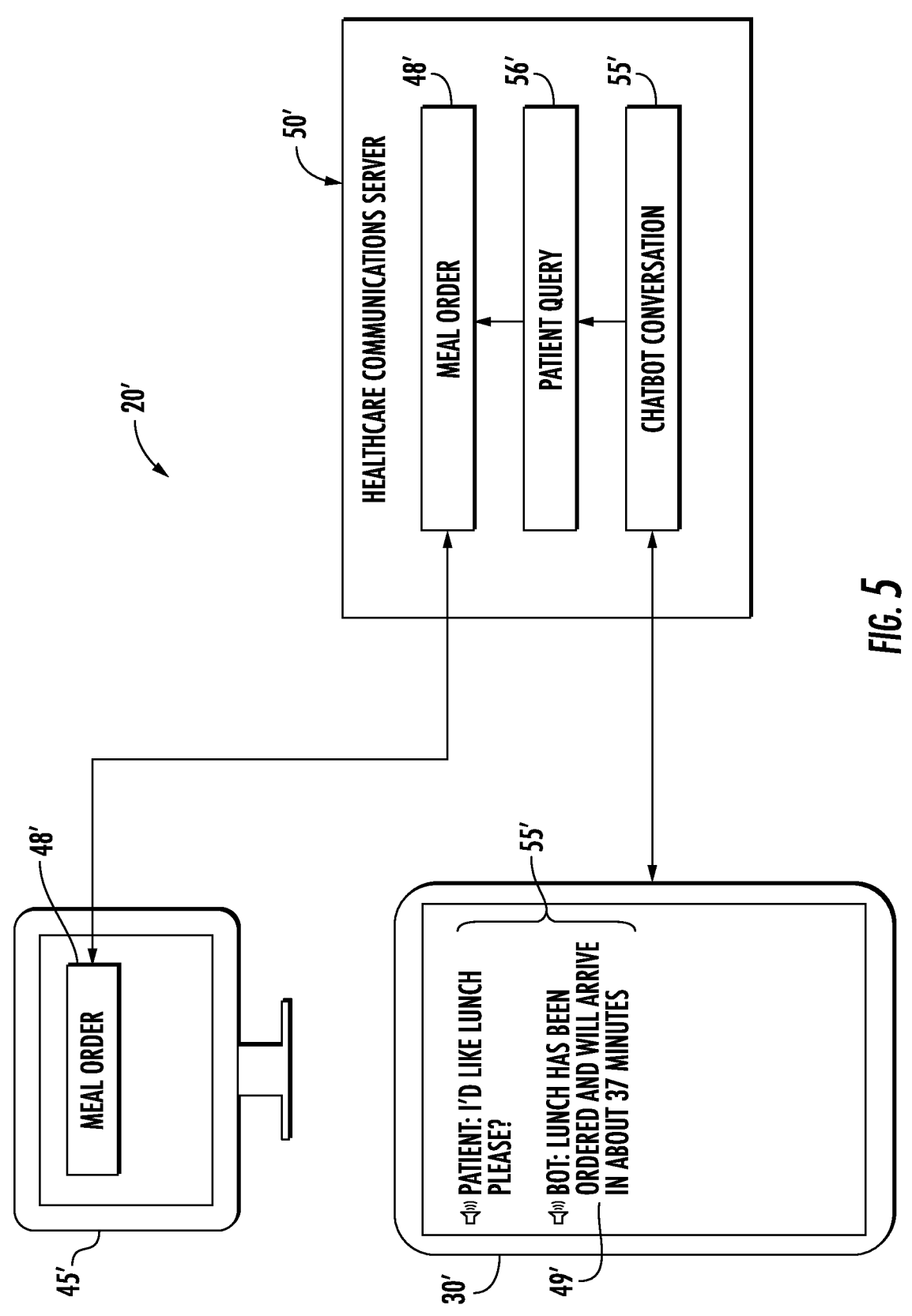
FIG. 5 is a schematic diagram of a healthcare communications system in accordance with another embodiment.

Referring now briefly to FIG. 5, in another embodiment,
the healthcare communications system 20' includes a meal
request interface device 45'. The meal request interface
device 45' may be in the form of a mobile wireless com-
munications device or other computer configured to operate
similarly to a restaurant computer system (e.g., in a kitchen)
whereby inbound meal requests are displayed and processed
for preparation, and the status of the meal preparation is
monitored. Notifications may be generated and communi-
cated that include the status of the meal request or prepa-
ration of the meal, and may be communicated to the patient,
requester, or other device.

The healthcare communications server 50', based upon
the chatbot conversation 55', generates and communicates a
meal order 48' to the meal request interface 45'. More
particularly, the healthcare communications server 50' may
respond audibly via the chatbot conversation 55' to a patient
query 56' (i.e., in the form of a meal request) for food (e.g.,
"I'm hungry", "What time is lunch?", or "Can I have some
food?"). The healthcare communications server 50' may
respond with a question of what the given patient would like
to eat or may request the given patient select from a list of
available meal items or food items.

Once the healthcare communications server 50' deter-
mines that a meal has been ordered or requested, the
healthcare communications server communicates the
desired meal or meal order 48' to the meal request interface
device 45' for preparation. As the preparation progresses on
the meal order 48' (i.e., cooking of the meal), the healthcare
communications server 50' may provide a meal order status
update 49' within the chatbot conversation 55'. For example,
the healthcare communications server 50' may audibly oper-
ate the chatbot conversation 55' to audibly provide the status
to the given patient. Exemplary statuses include "order
received", "in-progress", "preparing for delivery", "out for
delivery", and "delivered." A meal order status update 49'
may also include an estimated amount of time remaining
until the meal is delivered to the given patient. The health-
care communications sever 50' may determine the amount of
time remaining based upon a number of received and
generated meal requests along with their respective current
meal order statuses. For example, a relatively large amount
of meal requests near a same time (e.g., having a status of
"order received") may increase the amount of time remain-
ing for subsequent orders.

While a chatbot conversation with a given patient 22 has
been described, the embodiments of the healthcare commu-
nications system 20 described herein operates with multiple
patients each having a corresponding user interface device
30 and each having a corresponding audible chatbot con-
versation 55. Thus, updates to the initial chatbot conversa-
tion 54a may be updated based upon input from multiple
patients and their respective medical history data, medical
condition, and chatbot conversations.

A method aspect is directed to a method of healthcare
communications. The method includes using a healthcare
communications server 50 to obtain medical history data 23
associated with a given patient 22, and determine a medical
condition 24 of the given patient based upon the medical
history data. The method also includes using the healthcare communications server 50 to load an initial chatbot conversation script 54a associated with the determined medical condition 24, and audibly operate a chatbot conversation 55 with the given patient 22 via a user interface device 30 using the initial chatbot conversation script and based upon a voice activation command 36. The user interface device 30 is associated with the given patient 22 in a healthcare facility 21 and configured to listen for the voice activation command 36 from the given patient. The method further includes using the healthcare communications server 50 to generate and communicate a medical supply stocking list 58 for the healthcare facility 51 based upon the chatbot conversation 55 and the determined medical condition 24.

A computer readable medium aspect is directed to non-transitory computer readable medium for healthcare communications. The non-transitory computer readable medium includes computer executable instructions that when executed by a processor 51 cause the processor to perform operations that include obtaining medical history data 23 associated with a given patient 22, and determining a medical condition 24 of the given patient based upon the medical history data. The operations also include loading an initial chatbot conversation script 54a associated with the determined medical condition 24, and audibly operating a chatbot conversation 55 with the given patient 22 via a user interface device 30 using the initial chatbot conversation script 54a and based upon a voice activation command 36. The user interface device 30 is associated with the given patient in a healthcare facility 21 and configured to listen for the voice activation command 36 from the given patient 22. The operations further include generating and communicating a medical supply stocking list 58 for the healthcare facility 21 based upon the chatbot conversation 55 and the determined medical condition 55.

Figure 6:
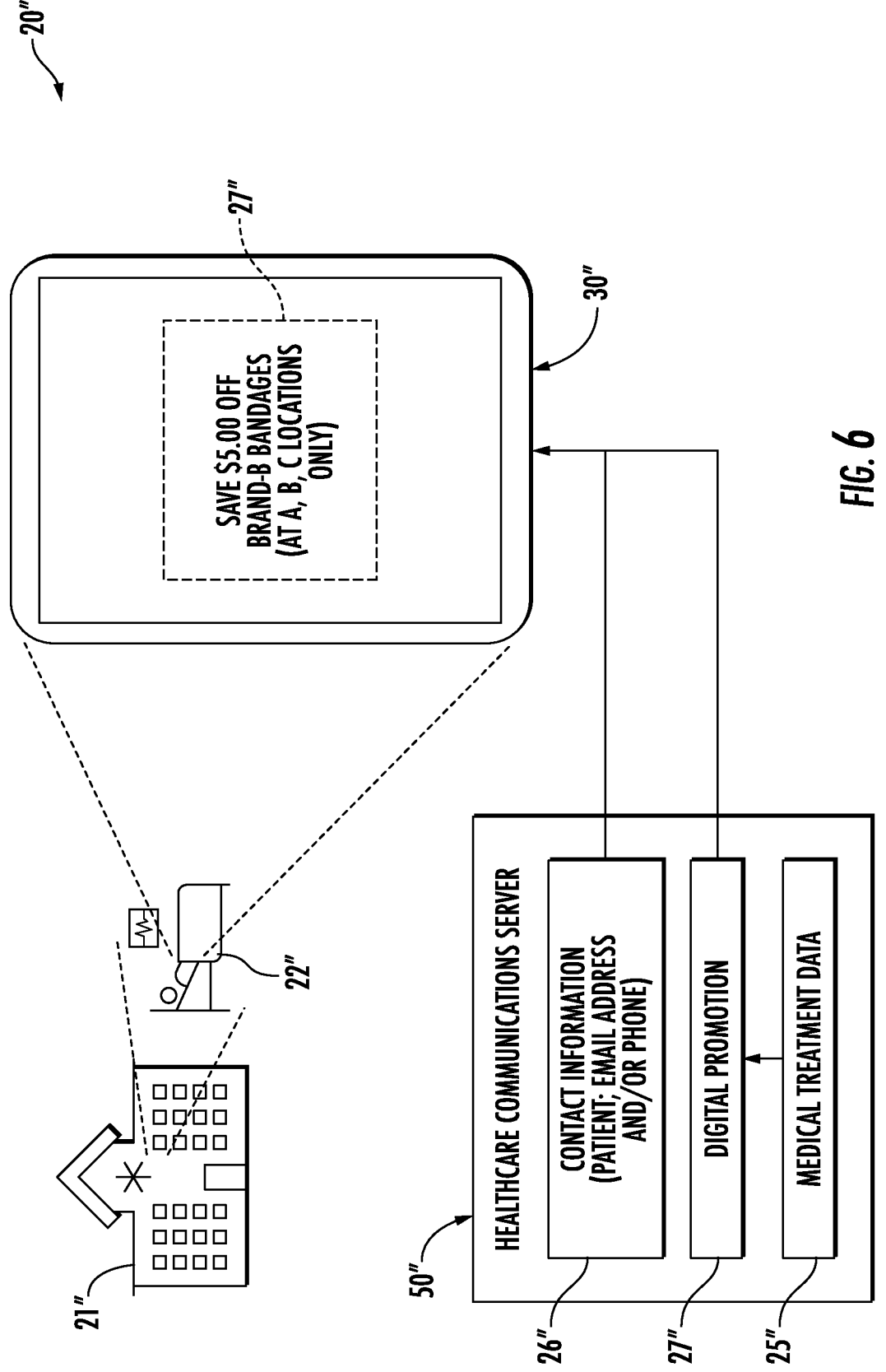
FIG. 6 is a schematic diagram of a healthcare communications system in accordance with another embodiment.
Figure 7:
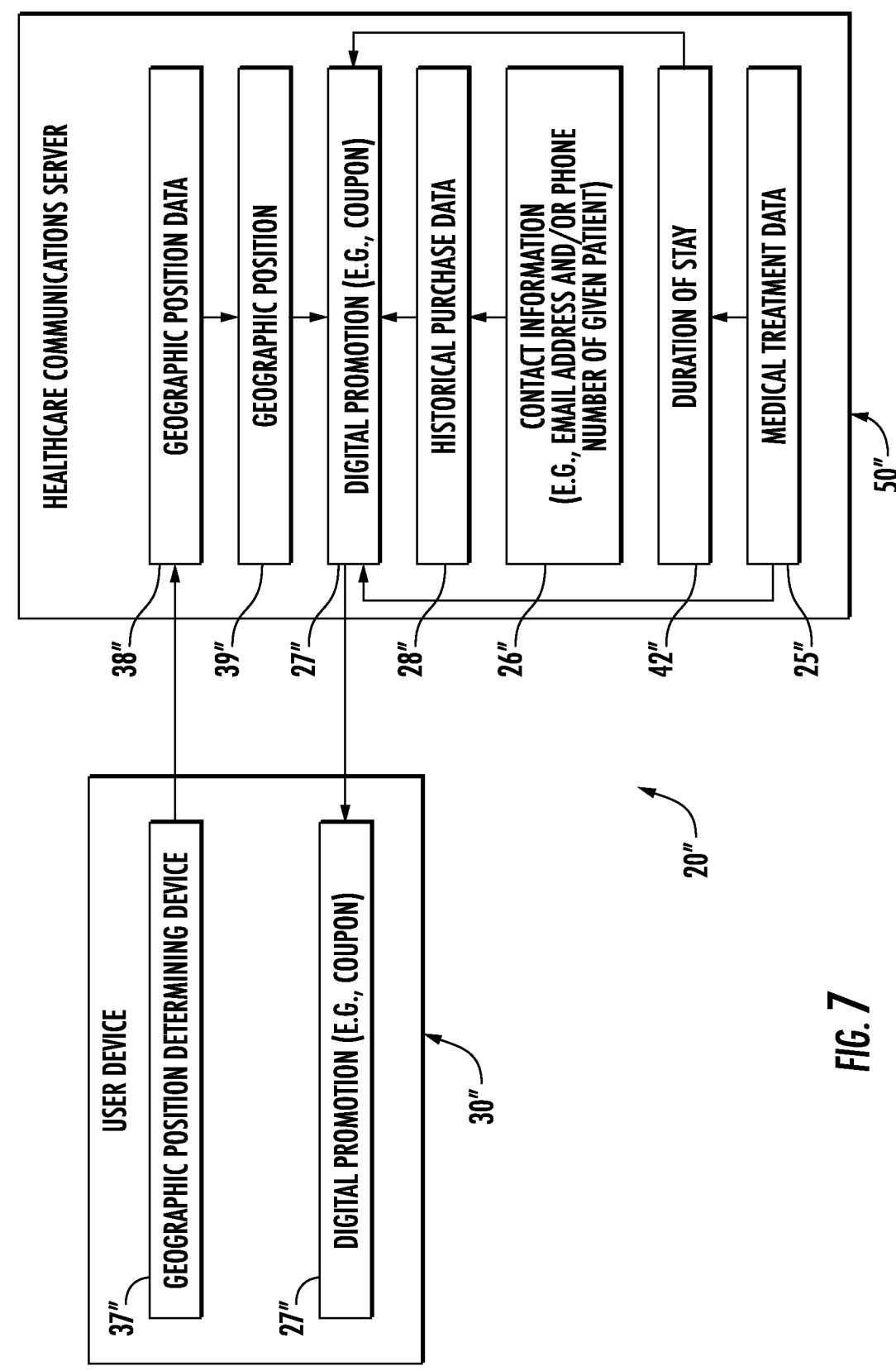
FIG. 7 is a schematic operational block diagram of a portion of the healthcare communications system of FIG. 6.

Referring now to FIGS. 6-8, in another embodiment, a healthcare communications system 20" includes a user device 30". The user device 30" is associated with a given patient 22", for example, as described above. The user device 30" is illustratively in the form of a mobile wireless communications device, and more particularly, a mobile phone. The user device 30" may be in the form of another device, such as, for example, a tablet computer. The user device 30" may function as, or be, the user interface device 30 described above.

The healthcare communications system 20" also includes a healthcare communications server 50". Similarly to the healthcare communications server described above, the present healthcare communications server 50" includes a processor 51" and an associated memory 52" cooperating therewith. While operations of the healthcare communications server 50" are described herein, the processor 51" and the memory 52" cooperate to perform the functions. Moreover, the healthcare communications server 50" may perform the functions of the healthcare communications server described above, and vice versa.

Referring now to the flowchart 160 in FIG. 9, beginning at Block 162, operations of the healthcare communications server 50" will now be described. At Block 164, the healthcare communications server 50" obtains medical treatment data 25" associated with a given patient 22" at a healthcare facility 21", which may be the same healthcare facility (e.g., building, campus, etc.) as described above. The healthcare communications server 50" may communicate with one or more healthcare facility servers or computers to obtain medical records or medical history data, as described above. For example, a unique patient identifier associated with the given patient 22" may be used to obtain the medical treatment data 25" (e.g., used as an index for retrieval). The medical history data, described above, may include the medical treatment data 25", for example, and include the determined medical condition or similar data, as described above.

The healthcare communications server 50" obtains contact information 26" associated with the given patient 22" (Block 166). Contact information 26" may include any one or more of an email address of the given patient 22" and a phone number of the given patient, for example. The contact information 26" may be obtained from the medical treatment data 25" or from other medical records, e.g., including the medical history data. The contact information 26" may be obtained from intake forms or other contact information provided by the given patient 22" upon or prior to admittance to the healthcare facility 21". The contact information 26" may also include names, phone numbers, email addresses, and/or other contact information for family members, care givers, other healthcare providers, or other non-patients, as will be appreciated by those skilled in the art.

At Block 168, the healthcare communications server 50" may optionally obtain historical purchase data 28", for example, associated with the given patient 22". The healthcare communications server 50" may obtain the historical purchase data 28" based upon the contact information 26". For example, the contact information 26", such as, for example, the name, email address, and/or phone number associated with the given patient 22" may be used as login credential (e.g., to a loyalty account that may associated with one or more retailers). The historical purchase data 28" may include previously purchased items, including item descriptions, unique item identifiers (e.g., stock keeping unit (SKU), universal product code (UPC), etc.), prices paid, dates and times of previous purchases, geographic locations of previous purchases, quantities of products purchased, and whether a digital promotion was used.

The healthcare communications server 50", at Block 170, may also optionally determine a geographic position of the given patient 22" by way of the user device 30". For example, the user device 30" may include a geographic position determining device 37" (e.g., a global positioning system (GPS) receiver) and communicate with the healthcare communications server 50" so that the healthcare communications server obtains geographic position data 38" from the geographic position determining device 37". The healthcare communications server 50" may determine a geographic position 39" of the user device 30" or given patient 22" based upon the geographic position data 38". The geographic position data 38" may include geographic coordinates relative to a geographic coordinate system, and the healthcare communications server 50" may determine the geographic position by applying the geographic coordinates to the geographic coordinate system and cross-referencing or comparing the geographic coordinates to known locations of businesses, restaurants, healthcare facilities, lodging, airports, grocery stores, etc.

The healthcare communications server 50" generates a digital promotion 27" redeemable toward a purchase based upon the medical treatment data 25" (Block 174). The digital promotion 27" is illustratively in the form of a digital coupon, for example, redeemable during a purchase transaction (e.g., at a point-of-sale (POS) device). The digital promotion 27" may be in the form of a digital rebate. The digital promotion 27" may be redeemable toward a product or service associated with the medical treatment data 25". For example, if the medical treatment data 25" includes data or information indicative of a special diet, the healthcare communications server 50" may generate the digital promotion 27" for food products (e.g., at a grocery store) that comply with the special diet (e.g., low fat, low sugar, low salt, etc.). If, for example, the medical treatment data 25" includes data indicative of a particular wound that requires a particular wound care, for example, the digital promotion 27" may be redeemable toward products to achieve a desired level of wound care (e.g., bandages, ointments, etc.).

The healthcare communications server 50" may generate the digital promotion 27" for redemption at a location adjacent the healthcare facility 21". For example, with respect to the example of the digital promotion 27" being redeemable toward specialized diet food products at a grocery store, the digital promotion may be redeemable at one or more grocery stores within a desired threshold distance from the healthcare facility 21", for example, 5 miles.

In embodiments where the user device 30" includes a geographic position determining device 37" and the healthcare communications server 50" obtains geographic position data 38" and determines a geographic position of the user device 39", the healthcare communications server may generate the digital promotion 27" to be redeemable at the location adjacent the healthcare facility 21" based upon the geographic position 39" of the user device 30". For example, the geographic position 39" of the user device 30" may be used to verify the location of the given patient and/or to define the threshold area adjacent the healthcare facility 21", which may include a location where the given patient resides.

The healthcare communications server 50" may alternatively or additionally, for example, when historical purchase data 28" is obtained, generate the digital promotion 27" to be redeemable toward a product or service based the historical purchase data. For example, the digital promotion 27" may be generated to be redeemable toward a particular brand of product or service favored by the given patient 22". Alternatively, the digital promotion 27" may be generated to be for a product or service that may typically not be selected by the given patient 22" as an incentive for the given patient to try another brand or product. Of course, the digital promotion 27" may be without consideration of geographic position 39" and/or the historical purchase data 28"

The given patient 22" may have an associated duration of stay 42" in the healthcare facility 21". The duration of stay 42" may be determined by the healthcare communications server 50" based upon the medical treatment data 25" and/or other data, such as, for example, medical history data. The healthcare communications server 50" may generate the digital promotion 27" to be redeemable toward a product or service during the duration of the stay in the healthcare facility 21". In other words, the healthcare communications server 50" may generate the digital promotion 27" to be valid during the duration, or stated alternatively, to have an expiration at the end the duration of the stay in the healthcare facility 21" (e.g., upon discharge from the healthcare facility). Of course, the healthcare communications server 50" may generate the digital promotion 27" to extend beyond the duration of stay 42" at the healthcare facility 21", which may also be based upon the medical treatment data 25".

The healthcare communications server 50", at Block 176, communicates, for example, wirelessly, the digital promotion 27" to the user device 30" based upon the contact information 26" associated with the given patient 21". The given patient 21" may, via input to the user device 30", save the digital promotion 27" to a digital wallet associated with the given patient, for example, or associated with user device 30".

In some embodiments, the healthcare communications server 50" may generate the digital promotion 27" upon discharge or to be redeemable upon discharge from the healthcare facility 21". The healthcare communications server 50" may determine discharge of the given patient 21" from the healthcare facility 22" based upon the medical treatment data 25" and/or the determined duration of stay 42" in the healthcare facility. Operations end at Block 182.

Figure 10:
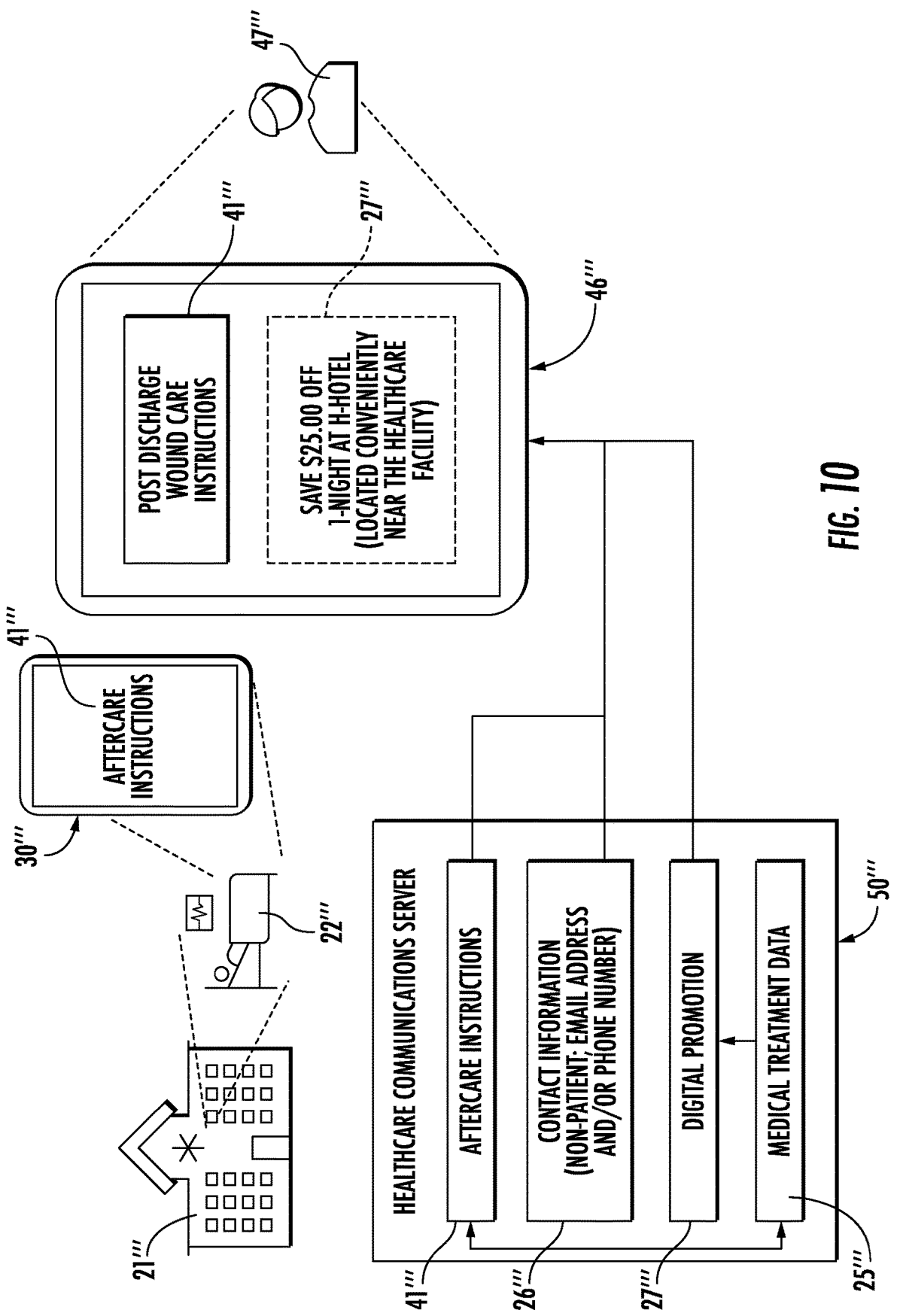
FIG. 10 is a schematic diagram of a healthcare communications system in accordance with another embodiment.

Referring now to FIG. 10, and the flowchart 260 in FIG. 11, beginning at Block 262, operations of a healthcare communications server 50''' in accordance with another embodiment will now be described. A user device 46''' may be associated with non-patient user 47''' associated with the given patient 22''', such as, for example, the family member, spouse, or caretaker. As will be appreciated by those skilled in the art, the user device 46''' may be different than the user device 30''' described in the embodiments above. The user device 46''' may be a mobile wireless communications device, for example, a smartphone, tablet, wearable computer, etc. Additionally, the contact information 26''' associated with the given patient 22''' may include the contact information for a family member, spouse, or caretaker, for example, the person associated with user device 46'''. The contact information 26''' may include an email address of the non-patient user 47''' and/or phone number associated with the non-patient user.

At Block 272, the healthcare communications server 50''' determines whether the given patient 22''' has been discharged from the healthcare facility 21'''. When or upon the given patient 22''' being discharged from the healthcare facility 21''' at Block 272, the healthcare communications server 50''' generates the digital promotion 27''' (Block 274). At Block 276, also when or upon the given patient 22''' being discharged from the healthcare facility 21''' at Block 272, the healthcare communications server 50''' communicates the digital promotion 27''' to the user device 46''' associated with the non-patient user 47''' based upon the contact information 26''' associated with the non-patient user. In other words, when the user device 46''' is that of family member, spouse, or caretaker, the digital promotion 27''' is communicated to their user device 47''' using their contact information 26''' obtained from the medical treatment data 25'''.

As will be appreciated by those skilled in the art, the healthcare communications server 50''' may generate the digital promotion 27''' to be redeemable toward a product or service based upon the medical treatment data 25''' and the non-patient user 47''', and more particularly, a product or service that may be more useful to the non-patient user as compared to the given patient 22'''. The digital promotion 27''' may thus be redeemable toward a purchase at a restaurant adjacent the healthcare facility 21''' and/or lodging adjacent the healthcare facility, which may be particularly useful if the non-patient user 47''' is frequently visiting the healthcare facility from locally or from further away (e.g., another state). The healthcare communications server 50''' may generate the digital promotion 27''' based upon other and/or additional factors, such as, for example, the geographic position of the user device 46''', obtained historical purchase data associated with the given patient and/or non-patient user 47''', upon discharge of the given patient 22''', and/or to be redeemable during a duration of stay at the healthcare facility 21''', as described above.

The healthcare communications server 50''' generates aftercare instructions 41''' based upon the medical treatment data 25''' (Block 278). The aftercare instructions 41''' may be in the form of written instructions, video instructions, or other type of instructions to seek and maintain care once the given patient 22''' is discharged from the healthcare facility 21'''. For example, if the medical treatment data 25''' is indicative of a wound, the aftercare instructions 41''' may include instructions for attending to the wound, supplies to purchase for the wound, and/or healthcare provider contact information, for example. The aftercare instructions 41''' may include other and/or additional information relating to the medical treatment. At Block 280, the healthcare communications server 50''' communicates the aftercare instructions 41''' to the user device 46''' associated with the given non-patient user 47'''. The healthcare communications server 50''' may alternatively or additionally communicate aftercare instructions 41''' to the user device 30''' associated with the given patient 22'''.

Operations illustrated at Blocks 264-270 and Blocks 274-276 are similar to the operations described above with respect to Blocks 164-170 and Blocks 174-176. Operations end at Block 282.

The operations of the user device 30''' may thus conceptually be considered independent of the operations as they relate to the user device 46'''. Of course, the healthcare communications server 50''' may also generate and communicate to the digital promotion 27''' to the user device 30''' associated with the given patient 21''', as described above.

A method aspect is directed to a healthcare communications method. The method includes using a healthcare communications server 50" to obtain medical treatment data 25" associated with a given patient 22" at a healthcare facility 21" and obtain contact information 26" associated with the given patient. The method also includes using the healthcare communications server 50" to generate a digital promotion 27" redeemable toward a purchase based upon the medical treatment data 25" and communicate the digital promotion to a user device 30" based upon the contact information 26" associated with the given patient 22".

A computer readable medium aspect is directed to a non-transitory computer readable medium for healthcare communications. The non-transitory computer readable medium includes computer executable instructions that when executed by a processor 51" cause the processor to perform operations. The operations include obtaining medical treatment data 25" associated with a given patient 22" at a healthcare facility 21" and obtaining contact information 26" associated with the given patient. The operations also include generating a digital promotion 27" redeemable toward a purchase based upon the medical treatment data 25" and communicating the digital promotion to a user device 30" based upon the contact information 26" associated with the given patient 22".

While several embodiments have been described herein, it should be appreciated by those skilled in the art that any element or elements from one or more embodiments may be used with any other element or elements from any other embodiment or embodiments. Many modifications and other embodiments of the invention will come to the mind of one skilled in the art having the benefit of the teachings presented in the foregoing descriptions and the associated drawings. Therefore, it is understood that the invention is not to be limited to the specific embodiments disclosed, and that modifications and embodiments are intended to be included within the scope of the appended claims.

That which is claimed is:

1. A healthcare communications system comprising:
a user interface device associated with a given patient in a healthcare facility and comprising an audio input device, an audio output device, and a controller coupled to the audio input device and the audio output device, the controller configured to cooperate with the audio input device to poll for input to the audio input device and apply speech recognition to determine whether a voice activation command from the given patient has been received;
a plurality of internet-of-things (IoT) devices within the healthcare facility and associated with the given patient, each IoT device operating according to a corresponding communications protocol;
at least one healthcare provider device associated with a healthcare provider at the healthcare facility;
a meal request device at the healthcare facility for receiving and displaying meal requests received from patients at the healthcare facility; and
a healthcare communications server configured to
obtain medical history data associated with the given patient,
determine a medical condition of the given patient based upon the medical history data,
load an initial chatbot conversation script associated with the determined medical condition,
cooperate with the user interface device to, upon receipt of the voice activation command, audibly operate a chatbot conversation with the given patient via the audio input and output devices of the user interface device to
cooperate with the audio input device to obtain a patient query, and
determine whether the patient query can be responded to using the initial chatbot conversation, and when so,
cooperate with the audio output device to audibly respond to the patient query using the initial chatbot conversation script,
determine whether the patient query is a request to operate a given one of the plurality of IoT devices, and when so, selectively operate the given IoT device based upon the patient query and according to the corresponding communications protocol,
determine whether the patient query is a request to be fulfilled by a healthcare professional, and when so, generate and communicate the request to the at least one healthcare provider device, and
determine whether the patient query is a request for a meal, and when so, generate and communicate the meal request to the meal request device for display thereat,
otherwise, when the patient query cannot be responded to using the initial chatbot conversation
operate as a communications bridge to establish a voice connection between the user interface device and the at least one healthcare device, and
update the initial chatbot conversation script with an updated chatbot conversation script from among a plurality of different updated chatbot conversation scripts by operating a machine learning algorithm that accepts as input thereto and is trained thereupon, the initial chatbot conversation with the given patient and different chatbot conversations associated with other different patients, and outputs therefrom the updated chatbot conversation script from among the plurality thereof, and generate and communicate a medical supply stocking list for the healthcare facility based upon the chatbot conversation and the determined medical condition.

2. The healthcare communications system of claim 1 wherein the healthcare communications server is configured to generate and communicate staffing levels for the healthcare facility based upon the chatbot conversation.

3. The healthcare communications system of claim 1 wherein the healthcare communications server is configured to provide a meal order status update within the chatbot conversation.

4. The healthcare communications system of claim 1 wherein the healthcare communications server is configured to poll the chatbot conversation for keywords each associated with a given updated chatbot conversation script, and update the initial chatbot conversation with the given updated chatbot conversation script based upon the keywords.

5. The healthcare communications system of claim 1 wherein the healthcare communications server is configured to pair each of the plurality of different updated chatbot conversations as query-response pairs, and input the query-response pairs into a classifier of the machine learning algorithm.

6. The healthcare communications system of claim 1 wherein the healthcare communications server is configured to operate the machine learning algorithm as a retrieval-based model.

7. The healthcare communications system of claim 4 wherein the healthcare communications server is configured to operate the machine learning algorithm to accept as input thereto, the keywords of the chatbot conversation.

8. The healthcare communications system of claim 1 further comprising a patient-listed contact device associated with a patient-listed contact of the given patient; and wherein the healthcare communications server is configured to, when the patient query can be responded to using the initial chatbot conversation, determine whether the patient query is a request to communicate with the patient-listed contact, and when so, obtain a contact identifier associated with the patient-listed contact from the medical history and establish communication between the user interface device and the patient-listed contact device based upon the contact identifier.

9. A healthcare communications server comprising:
a processor and an associated memory configured to
obtain medical history data associated with a given patient,
determine a medical condition of the given patient based upon the medical history data,
load an initial chatbot conversation script associated with the determined medical condition,
cooperate with a user interface device to, upon receipt of a voice activation command, audibly operate a chatbot conversation with the given patient via audio input and audio output devices of a user interface device associated with the given patient in a healthcare facility and configured to cooperate with the audio input device to poll for input to the audio input device and apply speech recognition to determine whether the voice activation command from the given patient has been received, the chatbot conversation being audibly operated to
cooperate with the audio input device to obtain a patient query, and determine whether the patient query can be responded to using the initial chatbot conversation, and when so,
cooperate with the audio output device to audibly respond to the patient query using the initial chatbot conversation script,
determine whether the patient query is a request to operate a given one of a plurality of internet-of-things (IoT) devices within the healthcare facility and associated with the given patient, and when so, selectively operate the given IoT device based upon the patient query and according to a communications protocol for operation of the given IoT device,
determine whether the patient query is a request to be fulfilled by a healthcare professional, and when so, generate and communicate the request to at least one healthcare provider device associated with a healthcare provider at the healthcare facility, and
determine whether the patient query is a request for a meal, and when so, generate and communicate the meal request to a meal request device for display thereat, the meal request device being at the healthcare facility and for receiving and displaying meal requests received from patients at the healthcare facility,
otherwise, when the patient query cannot be responded to using the initial chatbot conversation
operate a communication bridge to establish a voice connection between the user interface device and the at least one healthcare device, and
update the initial chatbot conversation script with an updated chatbot conversation script from among a plurality of different updated chatbot conversation scripts by operating a machine learning algorithm that accepts as input thereto and is trained thereupon, the initial chatbot conversation with the given patient and different chatbot conversations associated with other different patients, and outputs therefrom the updated chatbot conversation script from among the plurality thereof, and
generate and communicate a medical supply stocking list for the healthcare facility based upon the chatbot conversation and the determined medical condition.

10. The healthcare communications server of claim 9 wherein the processor is configured to poll the chatbot conversation for keywords each associated with a given updated chatbot conversation script, and update the initial chatbot conversation with the given updated chatbot conversation script based upon the keywords.

11. The healthcare communications server of claim 9 wherein the processor is configured to pair each of the plurality of different updated chatbot conversations as query-response pairs, and input the query-response pairs into a classifier of the machine learning algorithm.

12. The healthcare communications server of claim 10 wherein the healthcare communications server is configured to operate the machine learning algorithm to accept as input thereto, the keywords of the chatbot conversation.

13. The healthcare communications server of claim 9 wherein the processor is configured to, when the patient query can be responded to using the initial chatbot conversation, determine whether the patient query is a request to communicate with a patient-listed contact, and when so, obtain a contact identifier associated with the patient-listed contact from the medical history and establish communication between the user interface device and a patient-listed contact device based upon the contact identifier.

14. A non-transitory computer readable medium for healthcare communications, the non-transitory computer readable medium comprising computer executable instructions that when executed by a processor cause the processor to perform operations comprising:

obtaining medical history data associated with a given patient;

determining a medical condition of the given patient based upon the medical history data;

loading an initial chatbot conversation script associated with the determined medical condition;

cooperating with a user interface device to, upon receipt of a voice activation command, audibly operate a chatbot conversation with the given patient via audio input and audio output devices of a user interface device associated with the given patient in a healthcare facility and configured to cooperate with the audio input device to poll for input to the audio input device and apply speech recognition to determine whether the voice activation command from the given patient has been received, the chatbot conversation being audibly operated to cooperate with the audio input device to obtain a patient query, and determine whether the patient query can be responded to using the initial chatbot conversation, and when so, cooperate with the audio output device to audibly respond to the patient query using the initial chatbot conversation script, determine whether the patient query is a request to operate a given one of a plurality of internet-of-things (IoT) devices within the healthcare facility and associated with the given patient, and when so, selectively operate the given IoT device based upon the patient query and according to a communications protocol for operation of the given IoT device, determine whether the patient query is a request to be fulfilled by a healthcare professional, and when so, generate and communicate the request to at least one healthcare provider device associated with a healthcare provider at the healthcare facility, and determine whether the patient query is a request for a meal, and when so, generate and communicate the meal request to a meal request device for display thereat, the meal request device being at the healthcare facility and for receiving and displaying meal requests received from patients at the healthcare facility, otherwise, when the patient query cannot be responded to using the initial chatbot conversation operate a communication bridge to establish a voice connection between the user interface device and the at least one healthcare device, and update the initial chatbot conversation script with an updated chatbot conversation script from among a plurality of different updated chatbot conversation scripts by operating a machine learning algorithm that accepts as input thereto and is trained thereupon, the initial chatbot conversation with the given patient and different chatbot conversations associated with other different patients, and outputs therefrom the updated chatbot conversation script from among the plurality thereof, and generating and communicating a medical supply stocking list for the healthcare facility based upon the chatbot conversation and the determined medical condition.

15. The non-transitory computer readable medium of claim 14 wherein the operations comprise polling the chatbot conversation for keywords each associated with a given updated chatbot conversation script, and updating the initial chatbot conversation with the given updated chatbot conversation script based upon the keywords.

16. The non-transitory computer readable medium of claim 14 wherein the operations comprise pairing each of the plurality of different updated chatbot conversations as query-response pairs, and inputting the query-response pairs into a classifier of the machine learning algorithm.

17. The non-transitory computer readable medium of claim 14 wherein the operations comprise operating the machine learning algorithm to accept as input thereto, the keywords of the chatbot conversation.

18. The non-transitory computer readable medium of claim 14 wherein the operations comprise, when the patient query can be responded to using the initial chatbot conversation, determine whether the patient query is a request to communicate with a patient-listed contact, and when so, obtain a contact identifier associated with the patient-listed contact from the medical history and establish communication between the user interface device and a patient-listed contact device based upon the contact identifier.

\* \* \* \* \*